United States Patent [19]

Tolbert et al.

[11] 4,184,916
[45] Jan. 22, 1980

[54] CONTINUOUS CELL CULTURE SYSTEM

[75] Inventors: William R. Tolbert, Manchester; Joseph Feder, University City; Richard C. Kimes, Creve Coeur, all of Mo.

[73] Assignee: Monsanto Company, St. Louis, Mo.

[21] Appl. No.: 918,898

[22] Filed: Jun. 26, 1978

Related U.S. Application Data

[62] Division of Ser. No. 850,987, Nov. 14, 1977.

[51] Int. Cl.$^2$ ................................. C12K 9/00
[52] U.S. Cl. ..................... 435/241; 435/286
[58] Field of Search .......................... 195/1.8

[56] References Cited

U.S. PATENT DOCUMENTS

| | | | |
|---|---|---|---|
| 2,829,931 | 4/1958 | DePree et al. | 308/36.1 |
| 2,958,517 | 11/1960 | Harker et al. | 259/122 |
| 3,039,932 | 6/1962 | McLimans et al. | 195/1.8 |
| 3,241,675 | 3/1966 | Pashaian et al. | 210/73 |
| 3,572,651 | 3/1971 | Harker | 259/107 |
| 3,580,812 | 5/1971 | Bender et al. | 195/143 |
| 3,622,129 | 11/1971 | Mazowski | 259/107 |
| 3,647,632 | 3/1972 | Johnson et al. | 195/143 |
| 3,649,465 | 3/1972 | Scharf et al. | 195/143 |
| 3,850,748 | 11/1974 | Cook et al. | 195/1.8 |
| 3,905,865 | 9/1975 | McAleer et al. | 195/1.8 |
| 4,059,485 | 11/1977 | Tolbert et al. | 195/1.8 |

OTHER PUBLICATIONS

Glinos et al-J. Cell Physiol. vol. 79 (1971) pp. 79–80.
Himmelfarb et al-Science vol. 164 (May 2, 1969) pp. 555–557.
Thayer et al-Cancer Research vol. 30 (Jun. 1970) pp. 1709–1714.
Cook et al-In Vitro vol. 9 No. 5 (1974) pp. 318–322.
Lynn et al-Biotech, Bioeng. vol. XVII (1975) pp. 659–673.

*Primary Examiner*—Sam Rosen
*Attorney, Agent, or Firm*—Scott J. Meyer; James W. Williams, Jr.

[57] ABSTRACT

A cell culture system and apparatus is provided for the suspension culturing of mammalian cells in which fresh media can be added and spent medium filtered and withdrawn on a continuous or semi-continuous basis without cell disruption. The apparatus comprises a hollow flask assembly having a hollow shaft means journaled for rotation in a stationary sleeve sub-assembly and a filter unit suspended downwardly therefrom, said filter unit being in fluid communication with the top opening of the flask through the interior of said hollow shaft means and adapted for coaxial rotation with said shaft means.

1 Claim, 5 Drawing Figures

CONTINUOUS CELL CULTURE SYSTEM

This is a division of application Ser. No. 850,987, filed Nov. 14, 1977.

BACKGROUND OF THE INVENTION

This invention relates to a continuous cell culture system and apparatus therefor. More particularly, this invention relates to a flask assembly which can be used for suspension culturing of mammalian cells in which fresh medium can be added and spent medium can be separated from the growing cells by filtration and withdrawn from the flask on a continuous or semi-continuous basis.

In recent years there has been rapid growth in the development of various methods for the culturing of mammalian cells in suspension. The attainment of high cell densities is a primary objective of many of these approaches. The use of a cell culture vessel with controlled agitation by means of a magnetic stirrer bar or a mechanically driven impeller on a shaft is a typical feature of these methods. Examples of such apparatus are disclosed in U.S. Pat. Nos. 2,958,517; 3,039,932; 3,572,651; 3,622,129; and 3,649,465. These are essentially batch type spin culture devices in which the cells are incubated in a fixed amount of nutrient under appropriate culture conditions until cell growth has ceased.

It has been recognized that maintenance of constant levels of required nutrients coupled with removal of toxic cell by-products facilitates the propagation of cells in higher densities than is obtained in batch processes where the cells are grown in a fixed amount of nutrient and harvested after growth ceases. One approach to obtain such higher cell densities employs the batch type apparatus but involves daily centrifugation and resuspension of cells in fresh medium as reported by Clines et al, *J. Cell Physiol.* 79, 79–90 (1971). Another approach makes use of special apparatus developed for continuous suspension cell culturing. Examples of such apparatus developed for continuous suspension cell culturing are disclosed in U.S. Pat. No. 3,647,632; by Himmelfarb, *Science* 164, 555–57 (1969); and by Thayer et al, "Tissue Culture Methods and Applications" (Kruse and Patterson, editors), Academic Press, p. 345–51 (1973). The use of such devices in continuous cell culturing of various cell lines is further described by Thayer et al, *Cancer Res.* 30, 1709–14 (1970); Cook et al, *In Vitro* 9, 318–22 (1974); and by Lynn and Acton, *Biotech. Bioeng.* 27, 659–73 (1975).

Notwithstanding the advantages obtained with spin culture devices of the foregoing type, a problem which frequently exists is the presence of rotating bearing and seal surfaces which can contact the cells in the fluid suspension being agitated and thereby cause grinding and cell disruption at high cell densities. Placement of the rotating shaft driving means outside the culture vessel in order to avoid the grinding of cells in the flask introduces another problem, namely contamination by seepage into the vessel around the rotating shaft.

BRIEF SUMMARY OF THE INVENTION

In accordance with the present invention, an improved cell culture system and apparatus is provided for the suspension culturing of cells. This system comprises culturing in a flask assembly in which fresh medium can be added and spent medium can be separated from the growing cells by filtration and withdrawn from the flask on a continuous or semi-continuous basis. In this system and apparatus, no moving bearing or seal surfaces are present in the culture fluid which could contact the cells and thereby cause cell disruption, and no rotating shaft is extended through the top of the flask which could permit contamination from the outside to enter the flask during rotation of the shaft.

The apparatus of this invention thus comprises:
(A) a hollow flask having an opening at the top,
(B) an elongated hollow shaft means journaled for axial rotation in a stationary sleeve bearing assembly positioned within said flask, in fluid communication with said top opening and suspended downwardly from the top thereof,
(C) a self-supporting filter unit suspended downwardly from said shaft means and adapted for coaxial rotation therewith, said filter having
  (1) a fluid collection cavity in fluid communication with the interior of said shaft means and the top opening of said flask, and
  (2) a porous peripheral surface having a pore size smaller than the cells to be cultured or the carrier particles upon which said cells are attached.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

Figure 1:
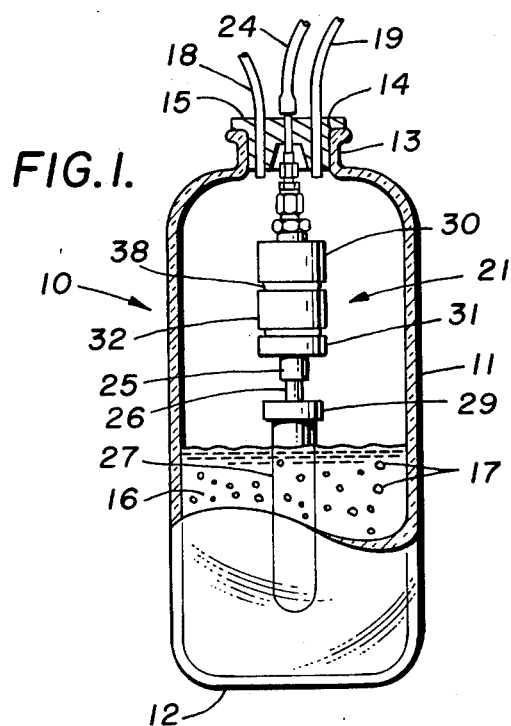
FIG. 1 is a side elevation view partly in cross section showing an embodiment of the flask assembly of the present invention.
Figure 2:
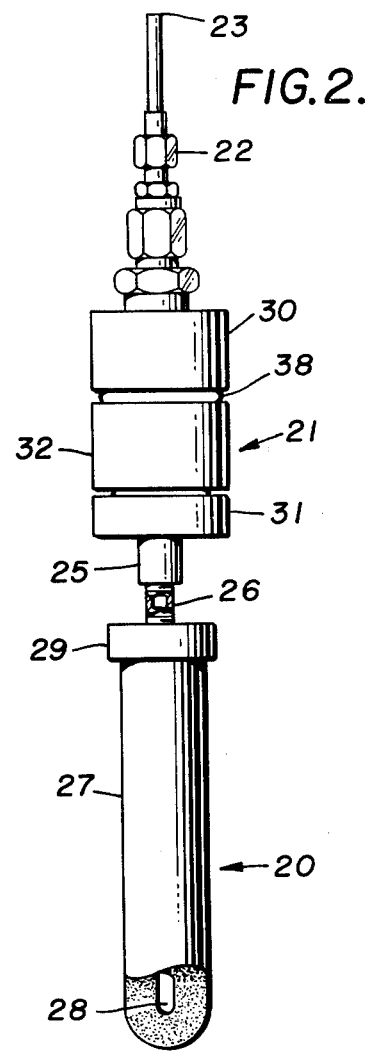
FIG. 2 is an enlarged said elevation view of the rotating filter unit of FIG. 1 suspended downwardly from the sleeve sub-assembly and tube connector means at the top.

Now with particular reference to FIGS. 1 and 2, reference numeral 10 refers generally to a flask which can be used for the continuous suspension culturing of mammalian cells. The flask preferably is made of clear glass or non-toxic rigid plastic materials but also can be made of biocompatible metals such as, for example, stainless steel. The flask is shown to have a generally cylindrical form with sidewalls 11, bottom 12, neck portion 13 and mouth 14. It will be appreciated, however, that other configurations of the flask can be employed. In FIG. 1, the mouth is shown to be closed with a removable stopper 15.

Flask 10 is shown be partially filled with culture fluid 16 in which the cells 17 are suspended. Tubes 18 and/or 19, which pass through holes in stopper 15 and thence into the interior of the flask, lead outwardly to a source of culture medium (not shown) which can be supplied to the flask on a continuous or semi-continuous basis. These tubes, or similar such tubes, also can be used for withdrawal of cells and cell culture fluid by vertical extension below the level of the culture fluid.

Positioned vertically within the flask is a rotatable filter unit 20 which is suspended downwardly from a stationary sleeve sub-assembly 21. The sleeve sub-assembly is held in stopper 15 by the tip portion 23 of connector 22 which leads to conduit 24 and thence to a fluid collection reservoir (not shown). Connector 22 can be, for example, a conventional Swagelok ® O-seal connector which also can be joined to an adaptor, as shown, to accommodate any specific diameter conduit 24.

Filter unit 20 is shown to be held in the sleeve sub-assembly 21 by attachment to an elongated hollow shaft 25 (seen in greater detail in FIG. 3) which, in turn, is journaled for rotation in the sleeve sub-assembly. Attachment of the filter unit and the sleeve sub-assembly is made by a threaded engagement of shaft 25 and a conduit 26. Other conventional types of fluid-tight fastening means also can be used for this attachment.

Filter unit 20 is shown to have a generally cylindrical body 27 which terminates with a rounded bottom and has an internal fluid collection cavity 28 and an opening in the top 29. The filter unit body can be made of microporous porcelain, sintered stainless steel, Teflon ® plastic or other such microporous filter materials which are fabricated to be sufficiently rigid to withstand rotation in use of the apparatus. For example, rotation may be at about 100 to 300 rpm during operation of the culture system. In FIG. 2 the thickness of the porous filter wall is shown partly in cross section at the bottom and exaggerated for emphasis.

The pore size of the filter should be smaller than the cells to be filtered, or the carrier particles upon which the cells are attached. In certain instances it is desired to filter all the cells while in other cases it is desired to filter only the attached cells. A pore size of from about $0.2\mu$ to about $7.0\mu$ is suitable for most single cells. In the case of cell aggregates or cells attached to microcarriers, the pore size can be larger but still smaller than the particles, for example, a pore size of about $25\mu$ to $75\mu$ in the case of particles of about $100\mu$ in diameter. The carrier particles can be materials such as Sephadex ® type ion exchange beads, silica glass particles and the like substances which are known to be useful for cell attachment in the suspension culturing of mammalian cells.

In a 3- or 4- liter size cell culture flask, the commercially available Selas Flotronics ® detachable metal-connector type porcelain filter candle FDM-126 S can be conveniently used as filter unit 20 with filter conduit 26.

Figure 3:
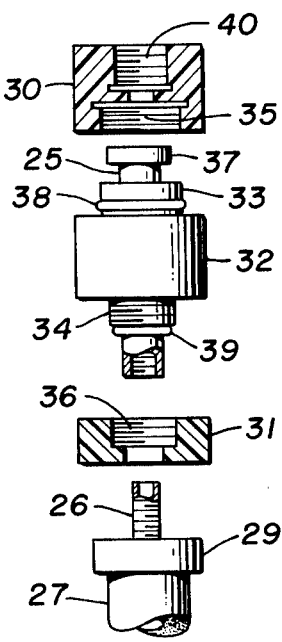
FIG. 3 is an exploded view of the sleeve sub-assembly of FIGS. 1 and 2 showing partial withdrawal of the hollow shaft means.

FIG. 3 shows the sleeve sub-assembly in greater detail. This sub-assembly comprises an upper part 30, a lower part 31 and a center part 32. These three parts, which comprise the sleeve sub-assembly, are shown to be generally cylindrical with a centrally disposed bore throughout the entire length. They are adapted for coupling together by threaded appendages 33 and 34 of the center sleeve part with threaded openings 35 and 36, respectively, of the upper and lower sleeve parts. Threaded opening 40 of upper sleeve part 30 is adapted for coupling to a threaded shank on connector 22. The bore of the center and lower sleeve parts is adapted for placement therein of the hollow shaft means 25 which is shown to be partially withdrawn in FIG. 3. Shaft 25 is seen to be provided with a flanged top 37 which is adapted for holding the shaft in the sleeve as it is seated on the top of center sleeve part 32. Upper sleeve part 30 preferably has an enlarged opening within its confines sufficient to accomodate the flanged top of shaft 25 (shown more clearly in the embodiment of FIG. 5). Shaft 25 is threaded internally at the lower end of the shank to provide a fastening means for engagement with the outer threaded portion of conduit 26 of the filter unit. Elastomeric O-ring seal 38 is positioned on the top appendage of the center sleeve part while a similar such seal 39 is positioned on the shank of shaft 25. These seals are adapted to prevent fluid leakage as the sleeve parts are held together as shown in FIGS. 1 and 2. Shaft 25 is thus adapted to rotate coaxially with filter unit 20 within the stationary sleeve sub-assembly 21.

Use of Teflon ® plastic materials for the fabrication of the shaft and sleeve sub-assembly parts or plastic coated steel parts provides suitable rotating seal surfaces which require no lubrication.

Figure 4:
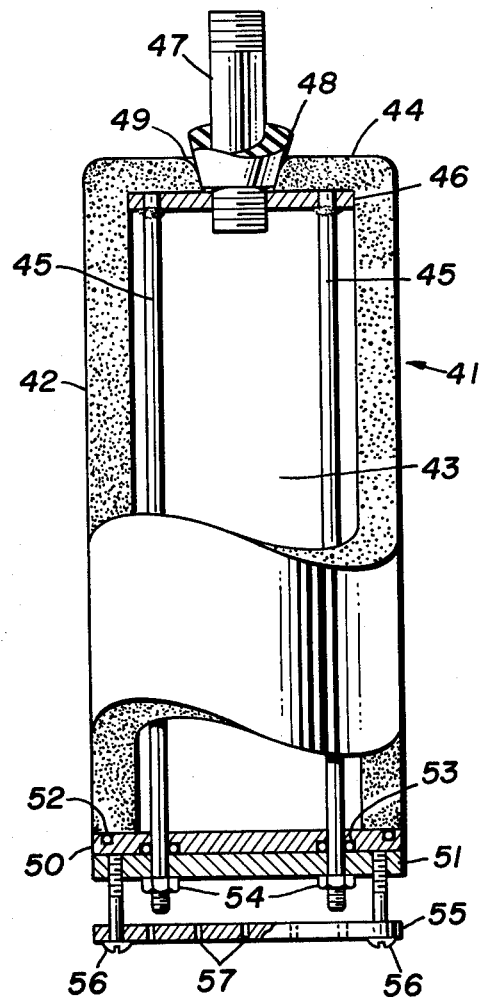
FIG. 4 is a side elevation view partly in cross section showing another embodiment of the rotating filter unit of the invention.
Figure 5:
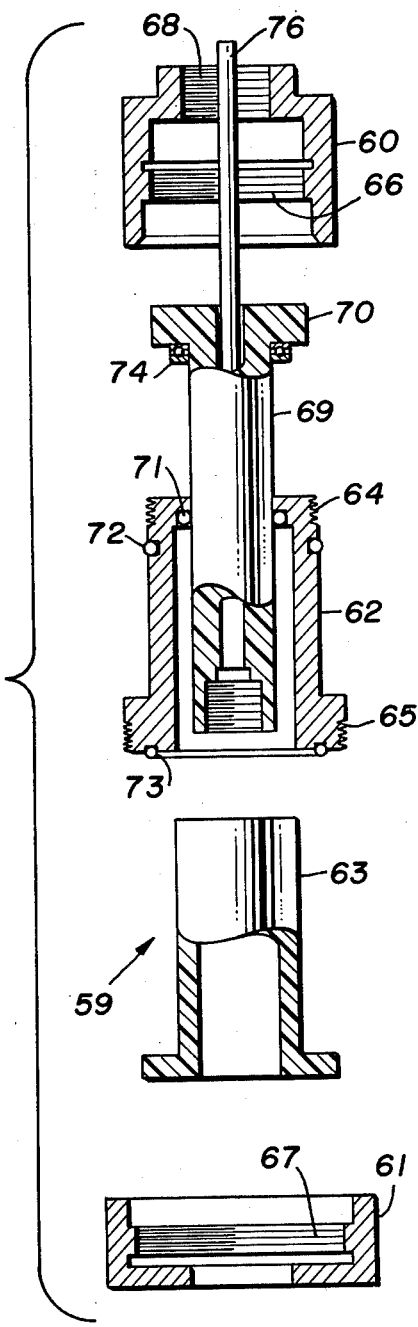
FIG. 5 is an exploded view of another embodiment of the sleeve sub-assembly of the invention.

In another embodiment of the invention shown in FIGS. 4 and 5, various modifications are incorporated in the filter unit and sleeve sub-assembly of the invention to provide greater rigidity and strength for large scale cell culture apparatus. In FIG. 4, filter unit 41 has a generally cylindrical body 42, an internal fluid collection cavity 43 and an opening in the top 44. Positioned within the fluid collection cavity are a plurality of reinforcement rods 45 which are suspended downwardly from an upper disc-shaped plate 46. These rods can be made of stainless steel or other such suitably rigid materials which are non-toxic to the fluid cellular product collected in the filter cavity. They are preferably welded onto plate 46 and extend to substantially the entire depth of cavity 43 as shown. In a preferred embodiment of the invention, four of these rods are employed in the filter unit which are equidistantly spaced apart circumferentially for appropriate balancing of the unit.

Plate 46 has a threaded opening at the center for engagement with the threaded shank of conduit 47. Conduit 47 is shown to be inserted through an elastomeric stopper 48 which is squeezed into the lip 49 of the filter opening as the conduit is threaded into plate 46 to provide an essentially leak-proof enclosure.

The cylindrical filter unit is closed at the bottom by a first bottom plate 50 and a second bottom plate 51. Plate 50 seals against the filter body 42 by an elastomeric O-ring seal 52 while plate 51 seals against the rods 45 by elastomeric O-ring seals 53. Plates 50 and 51 can be tightened into a sealing position by engagement of nuts 54 on the threaded ends of rods 45.

A third bottom plate 55 is positioned below the ends of rods 45 to serve as an attachment means for magnets (not shown). Plate 55 is shown to be fastened to plate 51 by screws 56. Small holes 57 drilled through plate 55 are adapted for removably wiring the magnets to the bottom of the filter unit.

It will be appreciated, of course, that other conventional fastening means can be used in place of those illustrated in FIG. 4.

In FIG. 5, the sleeve sub-assembly 59 comprises an upper part 60, a lower part 61, a center part 62, and a sleeve insert 63. These four parts, which comprise the sleeve sub-assembly, are shown to be generally cylindrical with a centrally disposed bore throughout the entire length. Parts 60, 61 and 62 are adapted for coupling together by threaded ends 64 and 65 of the center sleeve part with the threaded openings 66 and 67, respectively, of the upper and lower sleeve parts. Threaded opening 68 of upper sleeve part 60 is adapted for coupling to the threaded shank of a connector which can be, for example, similar to connector 22 in FIG. 1.

Sleeve insert 63 is adapted to frictionally engage the inner walls of center part 62 of the sleeve sub-assembly. The bore of this sleeve is adapted for placement therein of a hollow shaft means 69 which is shown to be partially withdrawn from the center sleeve part in FIG. 5. Shaft 69 is seen to be provided with a flanged top 70 which is adapted for holding the shaft in the sleeve as it is seated on the top rim of center sleeve part 62. Upper sleeve part 60 has an enlarged opening within its confines sufficient to accommodate the flanged top of shaft 69. Shaft 69 is threaded internally at the lower end of the shank to provide a fastening means for engagement of the upper threaded portion of conduit 47 of the filter unit. Elastomeric O-ring seal 71 is positioned at the upper inside wall of center sleeve part 62 and serves the same function as seal 39 in the embodiment of FIG. 3. A similar such seal 72 is positioned below the threaded portion at the upper outside wall of the center sleeve part while another similar such seal 73 is positioned under the foot of the center sleeve part. These three seals are adapted to prevent fluid leakage when the sleeve parts are sealingly assembled together in the manner shown in FIGS. 1 and 2. Shaft 69 is thus adapted to rotate coaxially with the filter unit 41 within the stationary sleeve sub-assembly 59.

It will be appreciated that additional O-ring seals can be employed in the apparatus of this invention, if desired. For example, a plurality of O-ring seals interspersed with annular rigid spacers can be positioned at the upper inside wall of center sleeve part 62 instead of the single O-ring seal 71.

Use of Teflon ® and Teflon glass filled plastic materials for the fabrication of the shaft and sleeve insert parts is preferred to provide suitable rotating seal surfaces which require no lubrication. In order to provide desired additional strength for large scale apparatus, the sleeve subassembly parts 60, 61 and 62 are preferably fabricated from stainless steel or other such suitably rigid materials which are non-toxic to cells and cell culture materials employed in operation of the apparatus.

When using a Teflon shaft and stainless steel sleeve parts, it is preferred to additionally employ a steel thrust bearing 74 on the underside of the flanged top of shaft 69 as shown to hold the weight of the filter unit suspended from the shaft. This bearing can be lubricated with a high-temperature silicone grease that is non-toxic to any cells that may come into contact with the grease. When the apparatus is provided with such a thrust bearing, a protective hollow tube also can be positioned within the bore of the sleeve assembly to prevent any fluid which rises during fluid withdrawal through the filter unit from contacting the bearing. For example, a glass tube 76 can be frictionally suspended from the inside of a connector such as connector 22 of FIGS. 1 and 2 and extended downwardly into the center sleeve part 62, preferably to about ¼ to ½ the depth of the center sleeve part.

In operation of the cell culture apparatus of this invention, using the embodiment of FIG. 1 for illustrative purposes, an inoculum of cells and a suitable culture medium are incubated in flask 10 under cell culture conditions which are appropriate for the particular cells used. Tubes 18 and 19 can be used to supply fresh culture medium to the flask continuously or at predetermined intervals. Magnetic bars (not shown) can be removably attached to the bottom of the outside of the filter unit which can then be caused to rotate by a revolving U-shaped magnet (not shown) positioned under the cell culture flask. The filter unit is preferably suspended to a depth in the flask such that it lies completely in the fluid medium. A vacuum drawn on line 24 by a peristaltic pump (not shown), which line is in direct fluid communication with the interior of the filter unit through the intermediately disposed hollow shaft means and sleeve sub-assembly, will cause withdrawal of fluid medium from the flask after passage through the microporous filter. Culture fluid can thus be separated from the residual cells on a continuous or semi-continuous basis. The fresh culture medium which is added through tubes 18 and 19 also can be monitored by a level controller (not shown) to maintain a constant level of suspension in the flask, if desired.

Cell culture apparatus of the present invention as described herein eliminates the usual need for a lower bearing surface in the flask below the upper level of the culture fluid. There are no moving bearing or seal surfaces in the flask assembly in contact with the suspension culture which could cause cell disruption at high densities. The filter unit is self-supporting and there are no moving seals between the filter unit and any filter support means which could contact the cell suspension. All seals within the filter unit are static. As no lower bearing is used, a centrally positioned solid shaft is not required within the filter unit and flow of effluent is not limited to an annular region around such shaft.

The cell culture apparatus of this invention can be used with conventional auxiliary apparatus such as pumping means for pumping in fresh medium from a supply reservoir and pumping out spent media, product, and toxic materials into an effluent collection reservoir. The flask can be provided with additional openings for gas inlet and outlet, sampling tubes and pH and liquid level monitoring probes. The entire flask assembly should be operated under sterile conditions throughout the cell growth period.

The cell culture apparatus of this invention also can be operated as a satellite flask in a series with other cell culture reactors by suitable tubing and pumping means. For example the present apparatus can serve as a filtering means for a main cell culture flask used for the growth of the cells.

In illustrative examples of the present invention using a 4-liter capacity cell culture flask in accordance with the apparatus of FIGS. 1 to 3 described hereinbefore, in 2 cell culture runs for over 100 hours each at 250 rpm, the runs were completed without any problems associated with cell disruption. Walker 256 Carcinosarcoma cells (ATCC No. CCL 38) converted to suspension growth were thus grown in Dulbecco's Modified Minimum Essential Medium (with 4.5 mg/ml of glucose) supplemented with 7% fetal calf serum. The cells were seeded at less than $10^6$ cells per ml and reached a maximum of $3 \times 10^7$ cells per ml with doubling times of 14 to 18 hours. More than 30 liters of media were passed through the filter in each run. Cells were healthy with high viability through long periods of log phase growth (up to 85 hours). These cells are useful for the production of tumor angiogenesis factor as is known from the publication by Folkman and Klagsbrun in Chapter 31 of "Fundamental Aspects of Neoplasia", at pages 401–412, edited by Gottlieb et al, Springer-Verlag, New York, 1975.

In further such illustrative cell culture runs using a 40-liter capacity cell culture flask provided with the filter unit and sleeve sub-assembly embodiments of FIGS. 4 and 5, the cells reached a maximum of $1.4 \times 10^7$ cells per ml in 120 hours without any problems associated with cell disruption.

In still another illustrative run, the 40-liter flask was operated as a chemostat in which the cell density was continuously held at a level of from $6 \times 10^6$ to $10 \times 10^6$ cells per ml during a 4 day culture period and in which cells and cell fluid were periodically harvested and fresh medium was periodically added as required. Cell fluid was thus withdrawn through the filter, and both cells and cell fluid were withdrawn unfiltered through an outlet tube such as tube 18 or 19. Such continuous harvesting permitted more cells and cell fluid product to be harvested in a given time than under conventional batch cell culture.

It will be appreciated that the continuous cell culture system of this invention is adaptable to any of the well-known tissue culture media such as, for example, Basal Medium Eagle's (BME), Eagle's Minimum Essential Medium (MEM), Dulbecco's Modified Eagle Medium, Medium 199, and balanced salt solutions (BSS) such as those of Earle and Hanks fortified with various nutrients. These are commercially available tissue culture media and are described in detail by H. J. Morton, *In Vitro* 6, 89–108 (1970). These conventional culture media contain known essential amino acids, mineral salts, vitamins and carbohydrates. They are also frequently fortified with mammalian sera such as fetal calf serum.

The present invention also is adaptable to all types of animal cells, including, for example, mammalian, fowl and amphibian cells. Primary cells taken from embryonic, adult or tumor tissues as well as cells of established cell lines can thus be used. Examples of typical such cells are primary rhesus monkey kidney cells, baby hamster kidney cells, pig kidney cells, embryonic rabbit kidney cells, mouse embryo fibroblasts, normal human lung embryo fibroblasts, HeLa cells, primary and secondary chick fibroblasts, and various cells transformed with SV-40 or polyoma virus.

Growth of these and other such cells in suitable nutrient culture media employing the continuous cell culture system of this invention can thereby be carried out in a manner to provide high cell densities without any moving bearing or seal surfaces contacting the cells which could cause cell disruption during the cell culture period.

Various other examples will be apparent to the person skilled in the art after reading of the disclosure herein without departing from the spirit and scope of the invention. All such further examples are included within the scope of the appended claims.

What is claimed is:

1. In the method of continuous cell culture comprising growing cells in an agitated liquid suspension of nutrient culture medium containing known amino acids, mineral salts, vitamins and carbohydrates and periodically removing filtered liquid from the cells, the improvement comprising carrying out the agitation and filtering in apparatus comprising a hollow flask having an opening at the top, an elongated hollow shaft means and a stationary sleeve assembly positioned within said flask, said elongated hollow shaft means journaled for axial rotation in said stationary sleeve assembly, in fluid communication with said top opening of said flask and supported downwardly therefrom without any lower bearing, and a filter unit supported downwardly from said elongated hollow shaft means without any lower bearing and without any moving seals between the filter unit and any filter support means which could contact the cell suspension and adapted for coaxial rotation with said elongated hollow shaft means, said filter having a fluid collection cavity in direct fluid communication with the interior of said shaft means and the top opening of said flask, and a porous peripheral surface having a pore size smaller than the cells to be cultured or the carrier particles upon which said cells are attached but sufficiently large to permit permeation of fluid into said fluid collection cavity.

* * * * *